(12) United States Patent
McCloskey et al.

(10) Patent No.: US 10,328,101 B2
(45) Date of Patent: Jun. 25, 2019

(54) INACTIVATION OF PAPILLOMAVIRUS

(71) Applicant: Jenny Colleen McCloskey, Mount Lawley, Western Australia (AU)

(72) Inventors: Jenny Colleen McCloskey, Mount Lawley (AU); Richard Alan Fox, Crawley (AU)

(73) Assignee: Jenny Colleen McCloskey, Mount Lawley, Western Australia (AU)

( * ) Notice: Subject to any disclaimer, the term of this patent is extended or adjusted under 35 U.S.C. 154(b) by 480 days.

(21) Appl. No.: 14/566,956

(22) Filed: Dec. 11, 2014

(65) Prior Publication Data

US 2015/0099011 A1    Apr. 9, 2015

Related U.S. Application Data

(62) Division of application No. 10/490,609, filed as application No. PCT/AU02/01312 on Sep. 25, 2002, now Pat. No. 8,939,932.

(30) Foreign Application Priority Data

Sep. 25, 2001 (AU) ........................ PR7909

(51) Int. Cl.
*A61K 33/00* (2006.01)
*A61K 33/18* (2006.01)
(Continued)

(52) U.S. Cl.
CPC ............ *A61K 33/18* (2013.01); *A61K 9/0031* (2013.01); *A61K 9/0034* (2013.01); *A61M 25/10* (2013.01);
(Continued)

(58) Field of Classification Search
CPC .............. A61M 3/0279; A61M 3/0295; A61M 25/1001; A61M 25/1002; A61M 31/00; A61M 2025/1052; A61M 2025/1061; A61M 2202/206; A61M 2210/1067; A61M 25/04; A61M 29/02; A61M 2210/1064; A61F 5/0093; A61F 2/958; A61F 5/445; A61F 5/451; A61B 17/42; A61B 5/4255; A61J 15/0038; A61J 15/0046
(Continued)

(56) References Cited

U.S. PATENT DOCUMENTS 694,971 A * 3/1902 Kistler .......................... 604/285
1,383,502 A * 7/1921 Vultee .......................... 604/279
(Continued)

FOREIGN PATENT DOCUMENTS

CA    1 313 803    2/1993
EP    088 714 A1    9/1993

OTHER PUBLICATIONS

Sokal, D.C. et al., "Inactivation of Papillomavirus by Low Concentrations of Providone-Iodine", *Sexually Transmitted Diseases*, 22(1): 22-24 (Jan.-Feb. 1995).

*Primary Examiner* — Scott J Medway
(74) *Attorney, Agent, or Firm* — Merchant & Gould P.C.

(57) ABSTRACT

A method of treating early papillomavirus infection of an orifice of a human or animal body including any canal associated with an orifice, comprising applying a viral inactivation agent to the orifice and/or canal in an amount effective to inactivate a portion of the virus infecting the orifice or canal. Apparatus is also disclosed.

3 Claims, 3 Drawing Sheets

(51) Int. Cl.
 *A61M 31/00* (2006.01)
 *A61K 9/00* (2006.01)
 *A61M 25/10* (2013.01)

(52) U.S. Cl.
 CPC ....... *A61M 31/00* (2013.01); *A61M 2025/105* (2013.01); *A61M 2025/1052* (2013.01); *A61M 2202/206* (2013.01); *A61M 2210/1067* (2013.01)

(58) Field of Classification Search
 USPC .................................. 604/41, 101.03, 103.07
 See application file for complete search history.

(56) References Cited

U.S. PATENT DOCUMENTS

| | | | | |
|---|---|---|---|---|
| 1,737,488 | A * | 11/1929 | Zohlen | 606/197 |
| 2,017,334 | A * | 10/1935 | Ackerman | 604/285 |
| 2,085,644 | A * | 6/1937 | Ferciot | 607/138 |
| 2,126,257 | A * | 8/1938 | Hird | 607/138 |
| 2,494,393 | A * | 1/1950 | Lamson | 600/29 |
| 2,687,131 | A | 8/1954 | Raiche | |
| 2,764,975 | A | 10/1956 | Greenberg | |
| 3,509,884 | A * | 5/1970 | Bell | 604/101.05 |
| 3,841,304 | A * | 10/1974 | Jones | 600/29 |
| 3,894,539 | A * | 7/1975 | Tallent | 604/57 |
| 3,900,033 | A * | 8/1975 | Leininger et al. | 606/193 |
| 3,916,897 | A * | 11/1975 | Elmore et al. | 604/179 |
| 4,337,775 | A | 7/1982 | Cook et al. | |
| 4,516,578 | A * | 5/1985 | Shuffield | 604/514 |
| 4,692,158 | A * | 9/1987 | Bloxom, Jr. | 604/260 |
| 4,976,692 | A | 12/1990 | Atad | |
| 5,035,883 | A | 7/1991 | Witkin | |
| 5,259,836 | A | 11/1993 | Thurmond et al. | |
| 5,312,343 | A | 5/1994 | Krog et al. | |
| 5,364,375 | A | 11/1994 | Swor | |
| 5,372,584 | A | 12/1994 | Zink et al. | |
| 5,451,232 | A * | 9/1995 | Rhinehart et al. | 606/192 |
| 5,476,095 | A * | 12/1995 | Schnall et al. | 600/423 |
| 5,509,427 | A * | 4/1996 | Simon et al. | 128/885 |
| 5,530,076 | A | 6/1996 | Eguchi et al. | |
| 5,536,243 | A | 7/1996 | Jeyendran | |
| 5,769,091 | A * | 6/1998 | Simon et al. | 128/885 |
| 5,906,575 | A * | 5/1999 | Conway et al. | 600/29 |
| 5,924,423 | A * | 7/1999 | Majlessi | 128/897 |
| 5,928,249 | A | 7/1999 | Saadat et al. | |
| 5,957,920 | A * | 9/1999 | Baker | 606/33 |
| 6,077,257 | A * | 6/2000 | Edwards et al. | 604/506 |
| 6,409,723 | B1 * | 6/2002 | Edwards | 606/41 |
| 6,419,673 | B1 * | 7/2002 | Edwards et al. | 606/41 |
| 6,425,853 | B1 * | 7/2002 | Edwards | 600/29 |
| 6,470,219 | B1 * | 10/2002 | Edwards et al. | 607/101 |
| 6,494,879 | B2 * | 12/2002 | Lennox et al. | 606/8 |
| 6,716,252 | B2 | 4/2004 | Lazarovitz et al. | |
| 7,022,103 | B2 | 4/2006 | Cappiello et al. | |
| 7,141,036 | B2 * | 11/2006 | Berman et al. | 604/60 |
| 7,291,129 | B2 * | 11/2007 | Li et al. | 604/164.01 |
| 8,016,816 | B2 * | 9/2011 | Gregory | 604/540 |
| 8,105,335 | B1 * | 1/2012 | Bentley | 606/127 |
| 8,500,771 | B2 * | 8/2013 | Isham | 606/197 |
| 2002/0019613 | A1 * | 2/2002 | Alexandersen | 604/279 |
| 2003/0028097 | A1 * | 2/2003 | D'Amico et al. | 600/427 |
| 2003/0120256 | A1 * | 6/2003 | Lary | A61M 25/00 604/509 |
| 2008/0300619 | A1 * | 12/2008 | Isham | 606/197 |

\* cited by examiner

INACTIVATION OF PAPILLOMAVIRUS

This application is a divisional of U.S. patent application Ser. No. 10/490,609 filed Aug. 24, 2004, which is a National Stage Application of PCT/AU02/01312 filed Sep. 25, 2002, which claims the benefit of priority to Australian Patent Application No. PR 7909 filed Sep. 25, 2001, all of which applications are hereby incorporated by reference in their entireties. To the extent appropriate, a claim of priority is made to each of the above disclosed applications.

FIELD OF THE INVENTION

This invention relates generally to the inactivation of papillomavirus and is concerned in particular with the in situ inactivation of human papillomavirus (HPV) in the uterine cervix and anal canal.

BACKGROUND OF THE INVENTION

Human papillomaviruses occur worldwide, affecting humans and the animal kingdom. Of the genital types affecting humans there are high and low risk types. The high-risk types are linked to the development of low and high-grade dysplasia and cervical cancer. Oncogenic strains of HPV have been found in 99.7% of cervical cancers. They are also associated with vulval, anal and penile carcinoma. Low risk types are associated with genital wart and low-grade dysplasia. Worldwide it has been estimated that 325 million women have either subclinical HPV or HPV-related clinical lesions.

The uterine cervix is particularly vulnerable to the effects of HPV infection at the transformation zone, which is an area where the stratified squamous cells of the vagina change over to become the columnar cells lining the endo-cervix and uterus. Cervical dysplasia can be either squamous or glandular in origin. Squamous dysplasia is more common, but the frequency of glandular lesions is increasing. The area of cell changeover is termed the metaplastic area, and most HPV associated cervical lesions occur within this area.

The presence of persistent HPV infection is thought to be p. prerequisite for the development and maintenance of second and third stage cervical intraepithelial neoplasia (CINIII), ie. severe or precancerous dysplasia.

Current treatment of severe uterine cervical dysplasia (squamous epithelial lesions or glandular) is by surgically removing the areas of the uterine cervix that may possibly be involved. Treatment initially requires cytology, colposcopy and biopsy, and then a surgical treatment such as laser excision, loop excision or cold coagulation of the uterine cervix.

Complications of surgical treatment of uterine cervical dysplasia include cervical stenosis, constriction and complete sealing of the os, pelvic endometriosis following hematometra, painful and prolonged menstruation, excessive eversion of columnar epithelium, infection, bleeding, pain, psychological morbidity, infertility, and an incompetent cervix. Disease may recur after treatment and even progress to invasive cancer. Some women are distressed by having Pap smear abnormalities even though they are not considered to be serious, and in order to alleviate their concerns, many women with low-grade lesions are unnecessarily treated. The other reason for unnecessary treatment of low grade lesions is the concern of the treating physician that the patient may fail to attend for further follow-up and consequently progress to high-grade disease.

No treatment for early HPV infection of the uterine cervix (i.e. where only the virus is detected and there are no clinically evident changes) is currently undertaken, and in most circumstances the diagnosis of early infection is discouraged, one of the reasons being lack of treatment. Current treatments are for the consequences of late stage changes in cells of the uterine cervix (CINI, CINII, CINIII), caused by human papillomavirus infection. Other chemical treatments of the uterine cervix are being explored, eg. imiquimod (a drug which acts by promoting the body's immune response to HPV) but as yet have not been reported as successful.

The anus is also particularly vulnerable to the effects of human papillomavirus infection, particularly at the transformation zone where the stratified squamous cells of the anal verge change over to the columnar epithelial cells of the rectum.

Current treatment for anal dysplasia is either surgical removal or, in many cases, observational if severe extensive infection is present. If the dysplasia is very severe and involves the whole circumference of the anal canal, surgical treatment is to remove the whole area and provide a colostomy. Because the operation is so radical, and the duration of time to progress from anal dysplasia to anal cancer is not known, an observational approach is usually undertaken and the individual treated when cancer arises. No treatment for early human papillomavirus infection (where only the virus is detected and there are no clinically evident changes) of the anal canal epithelium currently exists.

The skin of the vulva, penis and anal verge is commonly infected, and these are thought to be the sites from which infection spreads to genital orifices. No treatment is currently given for human papillomavirus infection of the skin when there are no clinical manifestations and dysplasia is absent. Laser ablation has been attempted previously but failed to eradicate the infection.

It is known that iodine in the form of povidone-iodine is effective in treating many viruses including bovine papillomavirus. The latter is reported in D. C. Sokal et al, "Inactivation of papillomavirus by low concentrations of povidone-iodine", Sexually Transmitted Diseases Vol 22, No. 1 (January-February 1995) 22-24, which suggests that povidone-iodine or other agents might reduce the rate of sexual transmission of the human papillomavirus associated with cervical cancer.

Povidone-iodine solution has relatively low tissue toxicity and has been used in topical formulations for disinfection, wound antisepsis, the treatment of burns, and the treatment of non-specific vaginitis. Povidone-iodine is available in over-the-counter preparations as a douche, vaginal gel, and vaginal suppository for the symptomatic treatment of minor vaginal irritation and itching.

By way of example, U.S. Pat. No. 5,035,883 discloses the use of povidone-iodine complex by applying an aqueous or aqueous alcoholic solution of the complex in the treatment of non-oral and non-periodontal human disorders. There is specific mention of vaginal infection and papillomavirus infection.

A form of iodine has been applied topically to the uterine cervix in the Schiller's test. In this test, Lugol's iodine is applied to the uterine cervix and the observed colour change is used to either detect HPV infected tissue or demarcate areas for treatment. The glycogen in fully differentiated genital epithelium takes up the iodine, staining the tissue dark brown. The application of iodine is used to distinguish between metaplasia (iodine negative) and HPV associated lesions (partial uptake).

A number of prior references describe intra-uterine catheters with single inflatable balloons, typically for sealing the entrance to the uterine cavity. For example, in Canadian patent 1,313,803, the balloon, which is inflated with the actual fluid being introduced into the uterine cavity, seals an extended region in the vicinity of the internal os. The devices of European patent publication 0088714 and U.S. Pat. No. 5,372,584 are generally similar save that the sealing balloon sits clearly within the uterine cavity immediately inwardly of the internal os.

An object of the present invention is to endeavour to reduce the incidence of uterine cervical dysplasia (all stages) and cervical cancers, and to avoid the more radical treatments of uterine cervical dysplasia, by treatment of early HPV infection of the uterine cervix.

A further object is to similarly endeavour to reduce the incidence of anal dysplasia and anal cancers.

SUMMARY OF THE INVENTION

The invention involves, in one respect, the concept of inactivating the human papillomavirus in and adjacent to the uterine cervical canal by application of a viral inactivation agent such as an iodine-containing substance.

In a further respect, the invention is extended to the treatment of HPV infections of other orifices of the human body, especially the anus.

In a first aspect, the invention provides a method of treating early human papillomavirus infection of an orifice of a human or animal body including any canal associated with an orifice, comprising applying a viral inactivation agent to the orifice and/or canal in an amount effective to inactivate a portion of the virus infecting the orifice or canal.

In a second aspect, the invention is directed to a method of preventing the development of a carcinoma or precancerous dysplasia in an orifice of a human or animal body including any canal associated with the orifice, comprising applying a viral inactivation agent to the orifice and/or canal in an amount effective to inactivate a portion of papillomavirus infecting the orifice or canal.

In a third aspect, the invention provides apparatus for treatment of early human papillomavirus infection of an orifice of a human or animal body including any canal associated with the orifice, comprising:
  stem means adapted for insertion along the orifice or canal;
  means carried by the stem means for occluding a distal restriction whereby to define a treatment cavity in the orifice and/or canal; and
  means to deliver an effective amount of an agent for inactivation of papillomavirus to said treatment cavity for application to the surfaces of the orifice and/or canal bounding said cavity.

In an advantageous application, the orifice and associated canal is a uterine cervix, most advantageously of a human female. For this application, the aforementioned distal restriction is the internal os and means is preferably further provided to occlude or sealingly cover the external os whereby the defined treatment cavity includes the external os and adjacent external vaginal wall surfaces comprising the upper vaginal vault, where the transformation zone between cervical and vaginal epithelium may occasionally extend.

In another application, the orifice and canal may be an anus, most advantageously of a human being. In this case, the external orifice is self-closing and the treatment cavity includes the transformation zone between colonic mucosa and the basal epithelial layer.

A preferred virus inactivation agent, especially for the purpose of inactivating human papillomavirus, is an iodine-containing substance. Suitable or effective such substances are thought to include povidone-iodine, and various other concentrations of available iodine.

The agent for inactivation of papillomavirus is preferably applied so that the agent infuses cell structure of the orifice or canal through to the basal cell layer where the reservoir of the HPV resides, and further infuses into the multitudinous gland structures and cavities in the walls of the endocervical canal. For this purpose, the agent for inactivation of papillomavirus is preferably applied under pressure.

Preferably, there is no hypersensitivity or allergic or other serious adverse reaction to the application of the viral inactivation agent to the orifice or canal.

The means for occluding the internal os or an internal point of the anal canal is preferably an expandable balloon. The stem means is advantageously of a co-axial tubular structure defining respective passages for the fluid to inflate the balloon and for infusion of the viral inactivation agent.

The means to occlude or sealingly close over the external os is preferably a cap which fits over the external os and adjacent cell structure and firmly engages the adjacent vaginal wall.

BRIEF DESCRIPTION OF DRAWINGS

The invention will be further described, by way of example only, with reference to the accompanying drawings, in which.

EMBODIMENTS OF THE INVENTION

Figure 1:
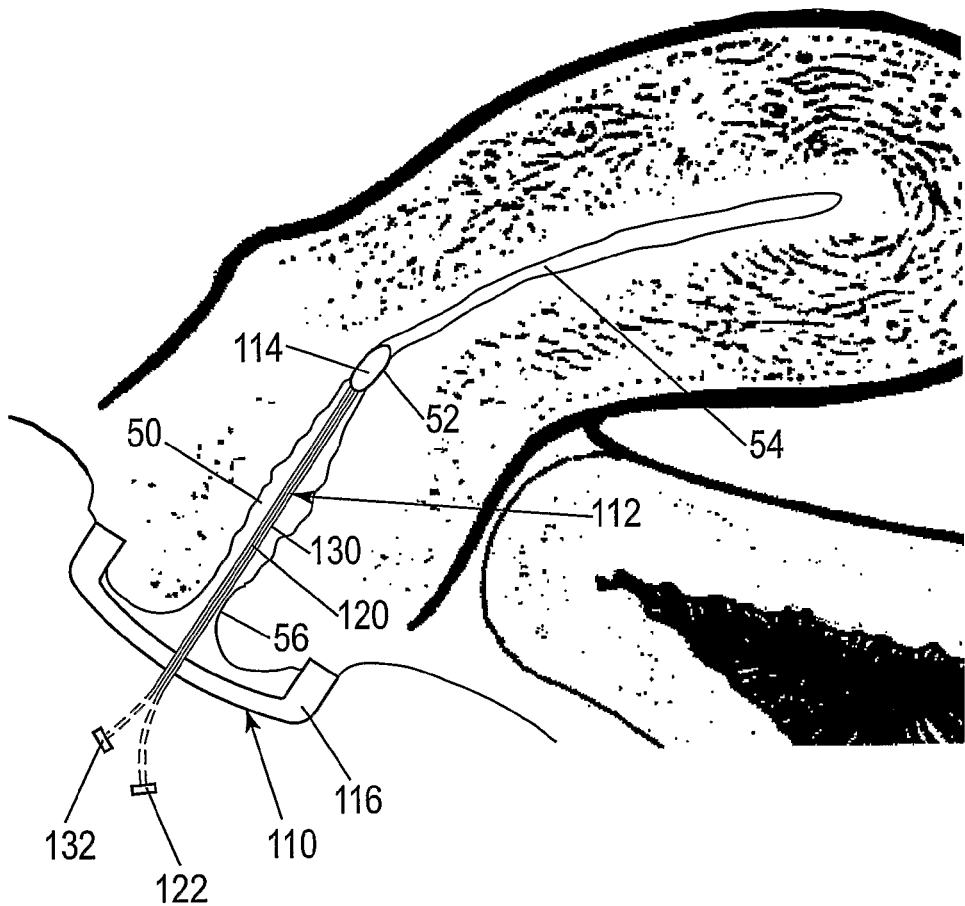
FIG. 1 is an in situ diagram depicting apparatus suitable for treatment of the human uterine cervix, in accordance with a first embodiment of the invention.

The illustrated apparatus 110 includes a co-axial stem 112 which carries an expansible balloon 114 at its inner or distal end and a cervical cap 116 at an intermediate location. The separation of balloon 114 and cap 116 is such that, when the device is inserted, with the balloon deflated, into the endocervical canal 50 until the cervical cap firmly engages the upper part of the vaginal vault about the external os 56, balloon 114 is in the region of the internal os 52 opening into the uterus 54 and at the distal end of the endocervical canal 50.

The inner or core tube 120 of stem 112 is employed to deliver an inflation fluid to the balloon, eg. a saline solution, by infusion to the tube from a syringe applied to a port 122. Agent for inactivation of human papillomavirus, as a suitable antiviral solution, is infused via the annular outer duct 130 of stem 112, again by application of a syringe to a port 132. The solution is infused to apply sufficient pressure to expand the canal to ensure that all surfaces including glandular surfaces are in close proximity to the solution including the ectocervix, the glandular endocervix and adjacent parts of the upper vaginal vault. It is thought that pressure cycling may be required to ensure that the solution in the canal remains at maximum concentration. The concentration and pressure of the solution is selected to ensure an effective virucidal concentration is achieved from the external epithelium to the basal cell layer.

It is thought likely that if the invention is employed to kill virus in areas of the uterine cervix which are already showing dysplastic change, such changes will subsequently reverse, since spontaneous regression of CIN lesions has been observed, with reversal documented more commonly in low grade lesions.

An important advantage of the invention is that the treatment is non-invasive and non-destructive. As the treatment is non-invasive, the integrity of the uterine cervix is maintained without the complications that occur with current surgical approaches, and indeed by early treatment the need for more radical treatments of uterine cervical dysplasia may be avoided. The treatment may be repeated where reinfection occurs. Because the preferred agent employed is inexpensive, it is anticipated that the treatment and treatment device would have wide-spread usage in both developed and under-developed countries. The device may be designed for a single use and subsequent discardal, or for re-use after intervening sterilisation.

Figure 2:
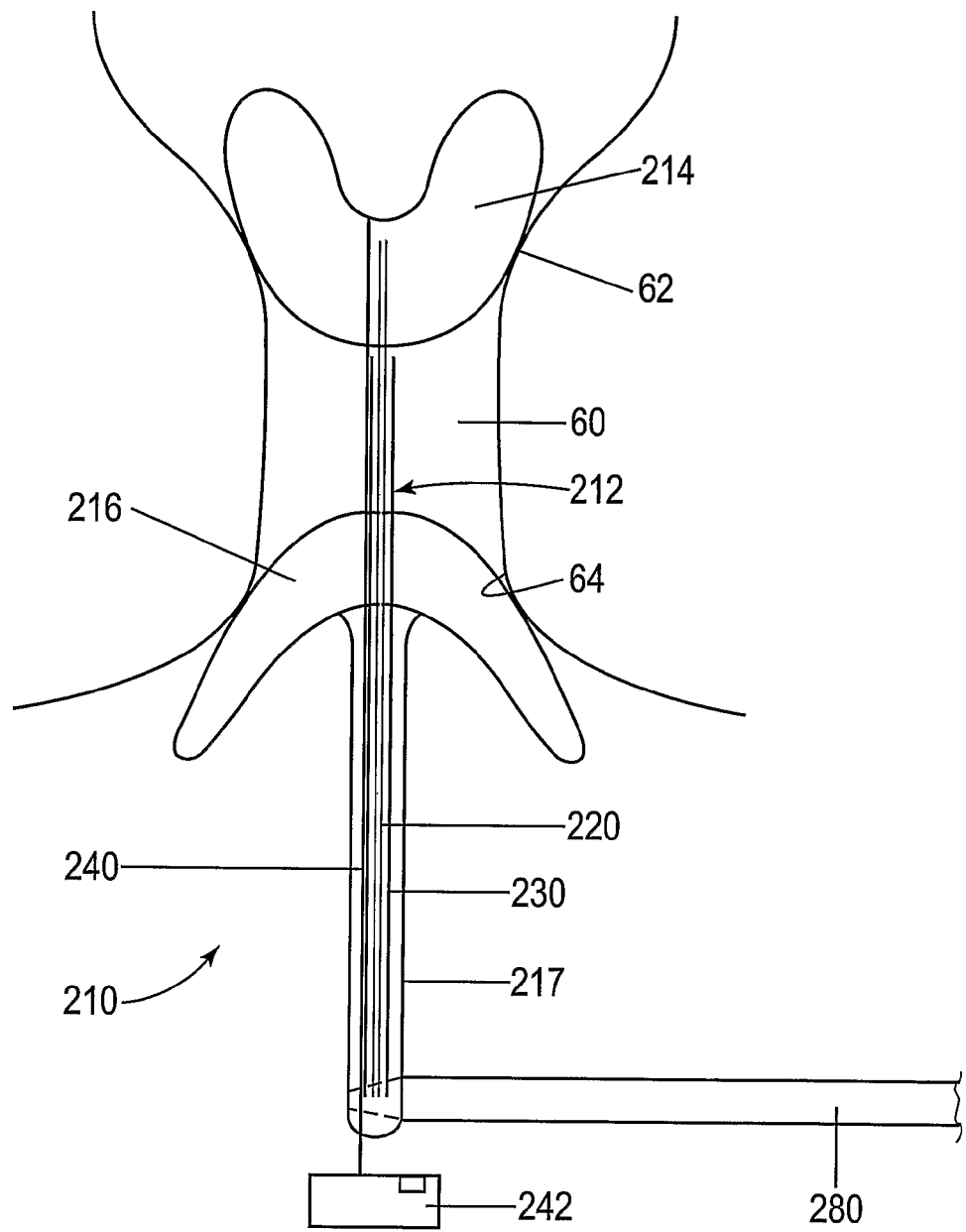
FIG. 2 is a similar diagram of an apparatus suitable for treatment of the human anus, in accordance with a second embodiment of the invention.

FIG. 2 illustrates a device 210 for anal treatment. In this diagram, like parts are indicated by like reference numerals in a "200" series. In this case, expansible balloon 214 is of course expanded to a larger size to engage the anorectal ring 62 at the inner end of the anal canal 60. There is advantageously a wire 240 on stem 212 providing a mechanism to retract the expanded balloon 214 to the illustrated V-shape, to collect pooled excess iodine. Instead of cap 116, outer occlusion means 216 is a conical plug to engage the anal verge 64, having a handle 217 to prevent the device being inserted too far. Artificial occlusion at the anal verge may not be necessary as the outer orifice is generally self-closing, but plug 216 nevertheless will assist in maintaining internal pressure while iodine is being administered.

Handle 217 may be engaged by a device 280 to stabilise the device and to apply pressure on the anal verge during iodine infusion. Device 280 may typically be attached to a treatment bed or chair similar to a gynaecological chair with an indent suitable to provide access to the anus.

It is thought desirable for iodine infusion into the anus to be administered when the axis of the anus is substantially vertical: this can be controlled by attaching a levelling device (example spirit level) to the handle 217.

It may be necessary to provide a tube to remove air from the anal canal or endocervical canal or vaginal vault as iodine is administered.

EXAMPLES (i) Preliminary

Many methods have been published for detecting human papillomaviruses from genital specimens. Thus far these have been one of two groups. The first are qualitative consensus or degenerate systems, which can detect a range of HPV types but have not been used to quantitate viral load. In these systems a group of primers is designed to accommodate as much of the sequence variation between types as possible. The second group of assays has been used to quantitate viral load and are limited, so far, to using type specific primers. Hence, while these can give sensitive and accurate results, they are limited in scope.

Using the SPF6 consensus primer set targeting the L1 ORF of the HPV genome, a wide range of virus types can be amplified. Using LightCycler technology the amplified products are detected by Sybr Green 1, a DNA specific fluorescent dye. The dye is non-specific, allowing the detection of any HPV type amplified by the primers, and the characterisation of the amplicon by melting curve analysis. The LightCycler platform also monitors the reaction in real-time, which allows quantitation of the target copy number.

The point at which the amplification signal rises above the background fluorescence, known as the crossing point, is determined for the samples and a range of plasmid standards. The crossing points of the standards are plotted against their known copy number on a semi-logarithmic scale to produce a linear standard curve. The crossing points of the samples are compared to this curve to generate quantitative viral loads. However this result is meaningless without normalisation, as there can be a wide variation in the amount of cellular material collected on a genital swab. To facilitate this the amount of cellular DNA in a sample, and hence the number of cells, is determined by a second quantitative PCR that targets the β-globin gene, which is present at two copies per cell. By this method, HPV viral loads can be expressed as viral copies per cell.

(ii) Treatment

Using a simplified treatment prototype, a sponge saturated with a solution containing iodine and connected to a reservoir of the treatment solution, this solution was applied to the ectocervix of three women for five minutes duration as an outpatient procedure. Each woman had a positive Digene Hybrid Capture 2 test for high risk strains of human papillomavirus prior to treatment and a detectable viral load from the cervix by the above described methodology. The women were clinically well with no underlying medical illness and no evidence of STD's (gonorrhoea, chlamydia, candidiasis, bacterial vaginosis, or HIV infection). The viral load swab was performed by placing a rayon tipped swab in the os of the cervix and rotating it once 360°. The transformation zone was clearly visible on the ectocervix for all treated women. In addition the women were asked to abstain from intercourse for six weeks after treatment. Following treatment the women were observed for 30 minutes and then reviewed 24 hours after treatment and then weekly for 6 weeks. Ongoing review at 3, 6, 9 and 12 months is occurring.

No serious untoward effects of treatment were experienced by any of the patients during or after treatment, or during the period of follow up, to date. Cramping of the uterus occurred in all three patients during, but not after, treatment and this was relieved by analgaesia. No evidence of clinical toxicity of the treatment solution has been demonstrated for a treatment duration of 5 minutes. Each patient had a slight increase in vaginal discharge following treatment, but no pain or discomfort after the treatment had been completed, or for the duration of follow up. The anatomy of the cervix remained normal after treatment, however some minor inflammation of the ectocervix and upper vaginal vault was evident in all patients at one week of follow up but had resolved by the second week. Thyroid function was normal at commencement in all three patients and has remained normal for up to 6 weeks of follow up in the first and second patients. The thyroid function in the third patient is normal at one week of follow up.

Figure 3:
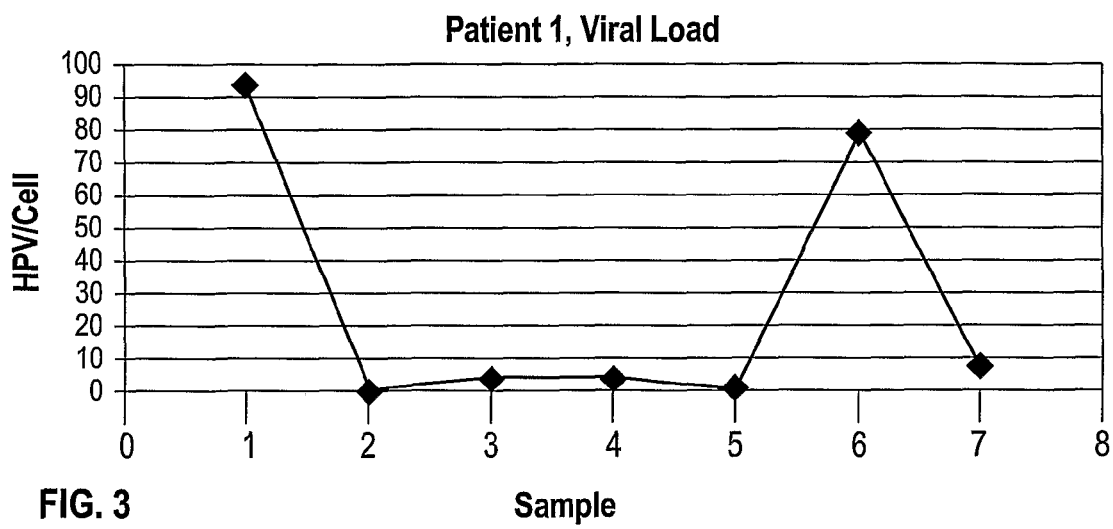
FIGS. 3 to 5 are graphical representations of cervical viral load observed in three patients over a period following treatment in accordance with an embodiment of the invention, set out in the examples hereinafter.
Figure 4:
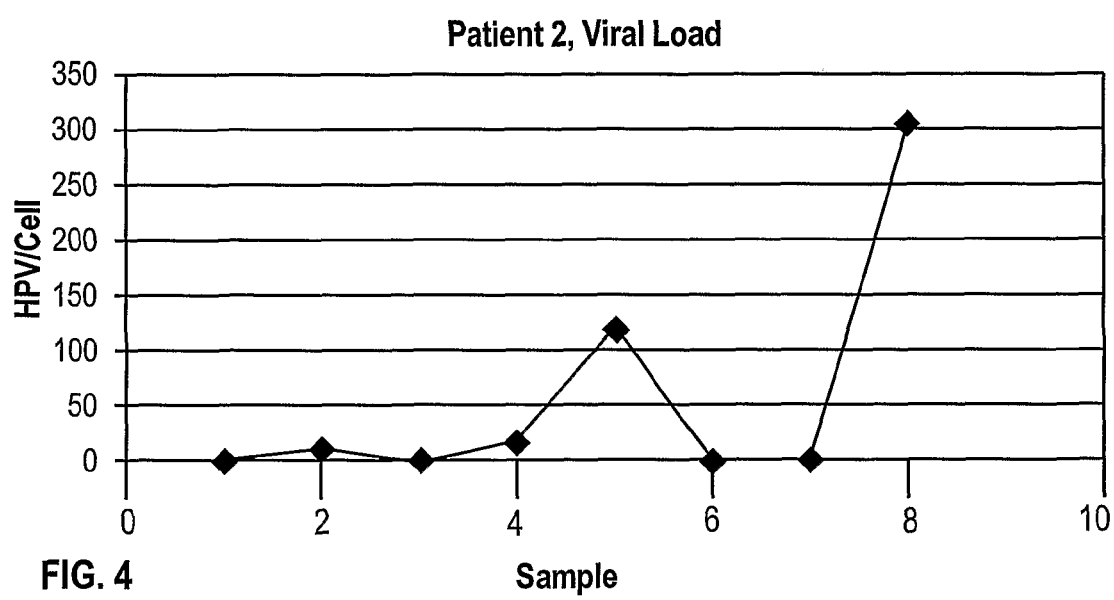
Figure 5:
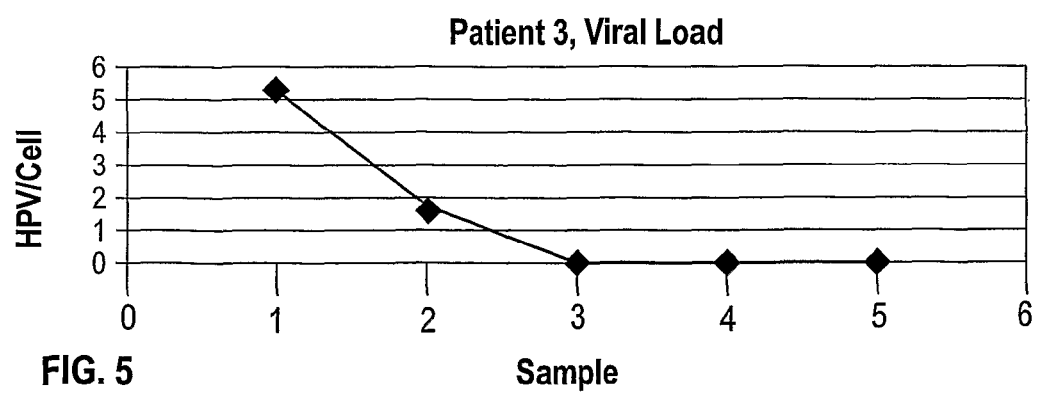

Results are provided in Tables 1 to 3 for the respective patients 1 to 3, and viral load is reported graphically in FIGS. 3 to 5 for patients 1 to 3 respectively.

(iii) Observations on Individual Patient Viral Load Data

Patient 1 showed a continual decrease in the Digene ratio over time, which was consistent to some extent with the viral load measurements over the treatment period (FIG. 3). No virus was detected at week 1 post treatment, and very low levels were detected at weeks 2, 3 and 4 post treatment compared to the level pretreatment. Only a single cervical swab was collected at each visit, so the sample variability in this patient cannot be assessed. A spike was seen 5 weeks after treatment and it was noted that the patient was menstruating at the time.

Patient 2 had a high Digene ratio (1706.5) three months prior to treatment, which had dropped significantly at the time of treatment (65.1). The viral load measurements (FIG. 4) were correspondingly low, and remained so until 3 weeks after treatment. At this time the viral load began to increase. No HPV could be detected on the samples at 4 and 5 weeks, however this may have been due to the low number of cells collected on these samples (demonstrated by low B-globin quantitation). The final sample at 6 weeks post treatment contained more cellular material and also gave a higher viral load quantitation than any previous sample. The Digene measurement (1241) at this point confirmed the increased amount of HPV present.

Patient 3 had a very low Digene ratio at the time of treatment and the majority of samples collected had no detectable HPV. Type specific probes will likely be necessary to detect HPV in these samples. This patient had a very large area of exposed cervical columnar epithelium occupying approximately 90% of the area of the ectocervix. It is significant in this patient that no clinical evidence of systemic toxicity of the administered treatment solution containing iodine was found, with thyroid function remaining normal at 1 week post treatment. In addition, no additional treatment complications were observed in this patient compared to the other two women. HPV was still detected 24 hours after treatment, but was less than the treatment value. HPV was not detected at week 1, 2 or 3 of follow up which is all that is available to date.

(iv) Summary

In summary, the data to date shows there has been a reduction in the number of HPV virus copies per cell after treatment, with the results being most impressive in the first patient. The number of viral copies per cell increased gradually during the follow up period for the first and second patients, suggesting the reduction in viral copies was not sustained. It is anticipated that with longer durations of treatment, deeper epithelial penetration of the treatment solution will occur and the treatment effect will be sustained longer. In addition, the three patients were treated with a simple prototype which is not treating the endocervical canal where some virus may reside. Improved and sustained results are anticipated with the treatment device illustrated in FIG. 1. As the treatment has been well tolerated in these three patients, with no significant side-effects or evidence of systemic toxicity it is expected the treatment will also be well tolerated for longer durations of treatment until the necessary treatment effect is achieved. No anaesthesia was given to the treated patients and it is anticipated the treatment will continue to be given on an outpatient basis.

TABLE 1

| | | | | | | | | | |
|---|---|---|---|---|---|---|---|---|---|
| | | | | | Patient 1 | | | | |
| Name | Date Of Birth | Sample | Digene | Sample Date | Sample | Lab No | B-globin | SPF (new test) | HPV/cell |
| Patient 1 | 25/12/1980 | Presentation | 134.15 18.43 | 13/02/2002 29/04/2002 | 1 | 624983E | 5319 | 186500 | 93.25 |
| | | 1 Week | | 07/05/2002 | 2 | 630101F | 124.5 | Not Detected | 0 |
| | | 2 Weeks | | 14/05/2002 | 3 | 634094X | 2038 | 7541 | 3.7 |
| | | 3 Weeks | | 22/05/2002 | 4 | 638604X | 540.6 | 2133 | 3.9 |
| | | 4 Weeks | | 28/05/2002 | 5 | 642488E | 172.5 | 233 | 1.35 |
| | | 5 Weeks | | 05/06/2002 | 6 | 647162P | 82.6 | 6456 | 78.1 |
| | | 6 Weeks | 2.37 | 11/06/2002 | 7 | 651336H | 351.7 | 2592 | 7.37 |

TABLE 2

| | | | | | | | | | | | | | | |
|---|---|---|---|---|---|---|---|---|---|---|---|---|---|---|
| | | | | | | | | | | | Patient 2 | | | |
| Name | Date Of Birth | Sample | Sample Date | Swab No | Digene | Lab No | B-globin | SPF (new test) | HPV/cell | Average | B-globin | PGMY (old test) | HPV/cell |
| | | | 19/04/2002 | 1 | 1706.5 | 620015A | 727 | 786000 | 1081 | | 727 | 255900 | 1279 |
| | | | 06/06/2002 | 1 | | | 1278 | 15470 | 77.35 | | 1278 | 28180 | 140.9 |
| Patient 2 | 07/03/1979 | Pre-treatment (1) | 01/07/2002 | 1 | | 663943J | 365.4 | 478.6 | 1.3 | 1.3 | 365.4 | Not detected | |
| TREATED 01/07/02 | | 1 Day (sample 2) | 02/07/2002 | 1 | 65.1 | 664720Y | 258.4 | 854.6 | 3.3 | 12.05 | 258.4 | Not detected | |
| | | | | 2 | | 664094E | 136.5 | 2849 | 20.8 | | 136.5 | Not detected | |
| | | 1 Week (3) | 09/07/2002 | 1 | | 668600D | 1922 | 1029 | 0.5 | 0.9 | 1922 | 3073 | 15.4 |
| | | | | 2 | | 668601K | 1808 | 2403 | 1.3 | | 1808 | 4352 | 21.8 |
| | | 2 Weeks (4) | 16/07/2002 | 1 | | 672878X | 100 | 4235 | 42.35 | 17.2 | 100 | 135800 | 1358 |
| | | | | 2 | | 672879D | 467.2 | 2357 | 5 | | 467.2 | 31800 | 159 |
| | | | | 3 | | 672880M | 207.6 | 934.5 | 4.5 | | 207.6 | 18580 | 89.5 |
| | | 3 Weeks (5) | 25/07/2002 | 1 | | 677934M | 3158 | 236200 | 75 | 116.5 | 3158 | 39810 | 199 |
| | | | | 2 | | 677935T | 3421 | 541500 | 158 | | 3421 | 84920 | 424.6 |
| | | 4 Weeks (6) | 30/07/2002 | 1 | | 680705P | 65 | Not detected | | 0 | 65 | Not detected | |

TABLE 2-continued

Patient 2

| Name | Date Of Birth | Sample | Sample Date | Swab No | Digene | Lab No | B-globin | SPF (new test) | HPV/cell | Average | B-globin | PGMY (old test) | HPV/cell |
|---|---|---|---|---|---|---|---|---|---|---|---|---|---|
| | | | | 2 | | 680706W | 82 | Not detected | | | 82 | Not detected | |
| | | | | 3 | | 680707C | 64 | Not detected | | | 64 | Not detected | |
| | | 5 Weeks (7) | 06/08/2002 | 1 | | 685785B | 160 | Not detected | | 0 | 160 | Not detected | |
| | | | | 2 | | 685784U | 15.8 | Not detected | | | 15.8 | Not detected | |
| | | | | 3 | | 684786H | 136 | Not detected | | | 136 | Not detected | |
| | | 6 Weeks (8) | 13/08/2002 | 1 | 1241 | 690357Y | 1545 | 1048000 | 678.3 | 308 | 1545 | 107300 | 536.5 |
| | | | | 2 | | 690358E | 211.8 | 24580 | 116 | | 211.8 | 23980 | 113.2 |
| | | | | 3 | | 690359L | 69.3 | 9127 | 132 | | 69.3 | 8057 | 116.8 |

TABLE 3

Patient 3

| Name | Date Of Birth | Sample Number | Digene | Sample Date | Lab No | SPF primers | B-globin | HPV/cell |
|---|---|---|---|---|---|---|---|---|
| | | | 7.52 | 22/05/2002 | 638956L | 25340 | 2886 | 8.7 |
| | | | | 13/08/2002 | | | | ~1 |
| | | | 18.06 | 23/08/2002 | 696493X | | | |
| Patient 3 TREATED 26/08/02 | 04/02/1972 | Presentation (1) | 1.51 | 26/08/2002 | 697766Y | Not Detected | 142.7 | 5.16 |
| | | | | | 697767E | Not Detected | 42.7 | |
| | | | | | 697768L | 1428 | 276.9 | 5.16 |
| | | 24 hours post (2) | | | 699024N | 4385 | 3769 | 2.19 | 
| | | | | | 699025U | 1492 | 1454 | 1.03 |
| | | | | | 699023G | Not Detected | 414.9 | 1.61 |
| | | 1 week (sample 3) | | 03/09/2002 | 703047G | Not Detected | 26300 | 0 |
| | | | | | 703045T | Not Detected | 866.8 | |
| | | | | | 703046A | Not Detected | 206.1 | |
| | | 2 Weeks | | 10/09/2002 | 707740F | Not Detected | 234.5 | 0 |
| | | | | | 707741M | Not Detected | 130.7 | |
| | | | | | 707742T | Not Detected | 129.8 | |
| | | 3 Weeks | | 17/09/2002 | 711857A | Not Detected | 48.3 | 0 |
| | | | | | 711858G | Not Detected | 121.2 | |
| | | | | | 711859N | Not Detected | 22.9 | |
| | | 4 Weeks | | | | | | |
| | | 5 Weeks | | | | | | |
| | | 6 Weeks | | | | | | |

The invention claimed is:

1. An anal treatment apparatus for treatment of early papillomavirus infection of an anal canal of a human body, comprising:
   a stem adapted for insertion along the anal canal, where the anal canal comprises an inner end and an opposing outer end, and further comprises an anorectal ring at the inner end and an anal verge at the outer end;
   an upper occlusion device and a lower occlusion device;
   wherein the upper occlusion device is a fluid expandable balloon carried by the stem that when expanded can occlude the anorectal ring at the inner end of the anal canal;
   wherein the lower occlusion device is a conical plug that can occlude the anal verge at the outer end of the anal canal;
   whereby the fluid expandable balloon when expanded and the conical plug are spaced and dimensioned to effectively engage and occlude the anorectal ring and anal verge, respectively, whereby to define a treatment cavity in the anal canal about the stem;
   a passage in the stem that can deliver fluid to the balloon to expand the balloon; and
   another passage in the stem that can deliver to the treatment cavity an effective amount of an agent for inactivation of papillomavirus for application to the surfaces of the anal canal bounding the treatment cavity.

2. The apparatus of claim 1, where the stem is a structure comprising a pair of co-axial tubes that define respective passages for conveyance of fluid to expand the fluid expandable balloon and for infusion of the viral inactivation agent.

3. The apparatus according to claim 1 wherein said conical plug has a handle.

* * * * *